United States Patent [19]

Sun et al.

[11] Patent Number: 5,028,613

[45] Date of Patent: Jul. 2, 1991

[54] NOVEL PYRROLOQUINOLINE ALKALOIDS AND METHODS OF USE

[75] Inventors: H. Howard Sun, Glenmoore, Pa.; Shin-ishi Sakemi, Aichi, Japan

[73] Assignee: Repligen Corporation, Cambridge, Mass.

[21] Appl. No.: 481,835

[22] Filed: Feb. 16, 1990

[51] Int. Cl.$^5$ .................. A61K 31/445; C07D 471/02
[52] U.S. Cl. ....................................... 514/292; 546/84
[58] Field of Search ........................... 546/84; 514/292

[56] References Cited

U.S. PATENT DOCUMENTS

| | | | |
|---|---|---|---|
| 4,548,814 | 10/1985 | Reinhart, Jr. | 424/95 |
| 4,729,996 | 3/1988 | Wright et al. | 514/215 |
| 4,737,510 | 4/1988 | Rinehart, Jr. | 514/388 |
| 4,808,590 | 2/1989 | Higa et al. | 514/272 |

OTHER PUBLICATIONS

Faulkner, D. J. (1984) Natural Products Reports 1:551–598.
Faulkner, D. J. (1986) Natural Products Reports 3:1–33.
Faulkner, D. J. (1987) Natural Products Reports 4:539–576.
Faulkner, D. J. (1988) Natural Products Reports 5:613–663.
Uemura, D., K. Takahashi, T. Yamamoto, C. Katayama, J. Tanaka, Y. Okumura, and Y. Hirata (1985) "Norhalichondrin A: An Antitumor Polyether Macrolide from a Marine Sponge," J. Am. Chem. Soc. 107:4796–4798.
Chemical Abstracts, vol. 111: 171348j Batzellines A, B and C. Novel Pyrroloquinoline Alkaloids from the Sponge Batzella sp. Sakemi et al. 11/89.

*Primary Examiner*—Mary C. Lee
*Assistant Examiner*—Joseph K. McKane
*Attorney, Agent, or Firm*—Saliwanchik & Saliwanchik

[57] ABSTRACT

The subject invention pertains to novel compounds, batzellines and isobatzellines, isolated from marine sponges. These compounds have been shown to possess antitumor activity. Various derivatives of these compounds have been prepared. The procedures for the isolation of the parent compounds and the preparation of some of their derivatives are described.

16 Claims, No Drawings

NOVEL PYRROLOQUINOLINE ALKALOIDS AND METHODS OF USE

BACKGROUND OF THE INVENTION

Considerable research and resources have been devoted to oncology and antitumor measures including chemotherapy. Tumors inflict mammals and man with a variety of disorders and conditions including various forms of cancer and resultant cancerous cachexia, which term refers to the symptomatic discomfort that accompanies the infliction of a mammal with a tumor. Such symptoms include weakened condition of the inflicted mammal as evidenced by weight loss, etc. The seriousness of cancer is well known since cancer is a major cause of death in man. While certain methods and chemical compositions have been developed which aid in inhibiting, remitting, or controlling the growth of tumors, new methods and antitumor chemical compositions are needed.

It has been found that some natural products and organisms are potential sources for chemical molecules having useful biological activity of great diversity. Marine life has been the source for the discovery of compounds having varied biological activities. Some of the United States patents which have issued for such inventions are as follows: U.S. Pat. No. 4,548,814 for didemnins, having antiviral activity, were isolated from a marine tunicate; U.S. Pat. No. 4,729,996 discloses compounds, having antitumor properties, that were isolated from marine sponges *Teichaxinella morchella* and *Ptilocaulis walpersi*; U.S. Pat. No. 4,808,590 discloses compounds, having antiviral, antitumor, and antifungal properties, isolated from the marine sponge Theonella sp.; and U.S. Pat. No. 4,737,510 discloses compounds, having antiviral and antibacterial properties, isolated from the Caribbean sponge *Agelas coniferin*. Clearly, marine sponges have proved to be a source of biological compounds, and a number of publications have issued disclosing organic compounds derived from marine sponges, including Scheuer, P. J. (ed.) *Marine Natural Products, Chemical and Biological Perspectives*, Academic Press, New York, 1978-1983, Vol. I-V; Faulkner, D. J., (1984) Natural Products Reports 1:551-598; Natural Products Reports (1986) 3:1-33; Natural Products Reports (1987) 4:539-576; Natural Products Report (1988) 5:613-663; J. Am. Chem. Soc. (1985) 107:4796-4798.

The present invention, utilizing sponges as a source material and supplemented by synthetic production methods, has provided the art with new biologically active compounds and new pharmaceutical compositions useful as antitumor and antimicrobial agents.

Other advantages and further scope of applicability of the present invention will become apparent from the detailed descriptions given herein; it should be understood, however, that the detailed descriptions, while indicating preferred embodiments of the invention, are given by way of illustration only, since various changes and modifications within the spirit and scope of the invention will become apparent from such descriptions.

BRIEF SUMMARY OF THE INVENTION

The invention provides new pyrroloquinoline alkaloids having useful biological activities. These compounds are known as batzellines and isobatzellines. Also provided are compositions containing such compounds, as well as methods for the preparation and use of the compounds and compositions.

The compounds of the subject invention can be represented by the following structural formula:

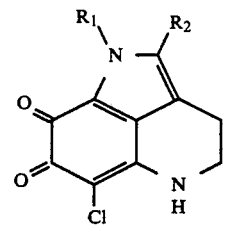

wherein $R_1$ can be $CH_3$ or H; and $R_2$ can be $SCH_3$ or H.

Further compounds of the subject invention can be represented by the following structural formula:

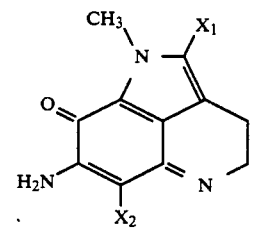

wherein $X_1$ can be $SCH_3$ or H; and $X_2$ can be Cl or H.

An additional compound of the subject invention is

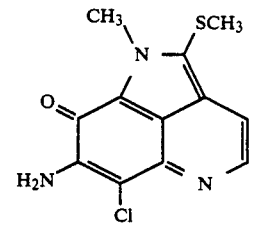

Specifically exemplified herein are batzellines A, B, and C, and isobatzellines A, B, C, and D. These compounds can be isolated from the marine sponge Batzella spp. as described below. The isobatzellines have been found to have antitumor and antimicrobial activity. Thus, these compounds and their derivatives can be useful as antimicrobial agents and in inhibiting the growth of tumor or cancer cells.

DETAILED DESCRIPTION OF THE INVENTION

The subject invention pertains to novel chemical compounds isolated from marine sponges. These compounds have been shown to possess antimicrobial and antitumor activity. Thus, the subject invention pertains to the compounds themselves, as well as pharmaceutical compositions containing these compounds. Also disclosed and claimed are methods for administering the novel compositions. Various derivatives of these compounds can be produced by known procedures. The parent compounds can be isolated from marine sponges as described below.

Isolation. The sponge from which the novel compounds were isolated has been assigned to the genus Batzella, as defined by Van Soest (Van Soest, R. W. M. [1984] "Marine Sponges from Curacao and Other Caribbean Localities. Part III. Poecilosclerida. Stud.

Fauna Curacao Caribb. Isl. 66(199):167 pp.). The sponge has been found at the following locations: off Lucaya, Grand Bahama Island (latitude 26°31.75′ N, longitude 78°31.60′ W) at a depth of 387 feet; and off West End, Grand Bahama Island (latitude 26°41.67′ N, longitude 79°00.60′ W) at a depth of 420 feet, attached to a rock on a sand/mud slope. The sponge is classified as follows:

| Phylum | Porifera |
|---|---|
| Class | Demospongiae |
| Order | Poecilosclerida |
| Family | Demascididae |
| Genus | Batzella |

The Batzella from which the novel compounds of the subject invention are isolated has the following characteristics: They are small black sponges, amorphous to spherical, tan or light brown in ethanol. They have a detachable ectosome, a plumo-reticulate choanosomal skeleton, and tangential ectosomal skeleton of strongyles of one size category. Many of the strongyles have malformations, as described by Van Soest (1984, supra) for *Batzella rosea*. There are no microscleres. The consistency is compressible. Related genera include Strongylacidon and Chondropsis, both of which have a plumose or plumoreticulate skeleton of strongyles. Microscleres (chelae and sigmas) are usually present in these genera, but could be rare or absent (Bergquist, P. R. and P. J. Fromont [1988] "The marine fauna of New Zealand: Porifera, Demospongiae, Part 4 (Poecilosclerida). N. Z. Oceanographic Inst. Mem. 96:197 pp.). These Batzella share skeletal characteristics with all three genera. Chondropsis incorporates sediment into its skeleton and, as a result, has a reduced complement of both megascleres and microscleres. These Batzella incorporate a small amount of sediment, but appear to have a normal quantity of spicules. They have, therefore, been assigned to the genus Batzella on the basis of their plumo-reticulate architecture, detachable ectosome, presence of strongyles (many of which are malformed), and lack of microscleres.

Following are examples which illustrate procedures, including the best mode, for practicing the invention. These examples should not be construed as limiting. All percentages are by weight and all solvent mixture proportions are by volume unless otherwise noted.

EXAMPLE 1—ISOLATION OF NOVEL COMPOUNDS

A frozen sample (68 g) of Batzella sp. was extracted with 2:1 methanolchloroform (200 ml×4). The extract was concentrated in vacuo and additional water was added to give an aqueous suspension (100 ml) which was further extracted with ethyl acetate (100 ml×4).

This extract (670 mg) was fractionated by countercurrent chromatography on an Ito multi-layer coil planet centrifuge (CPC) with heptane-EtOAc-MeOH-H$_2$O (4:7:4:3, lower phase stationary). The stationary phase was rechromatographed on the CPC (heptane-EtOAc-MeOH-H$_2$O, 2:7:6:3, lower phase stationary) to yield a pure compound, batzelline A 1, 0.16% of wet weight sponge, and a fraction containing two minor components. Subsequent countercurrent chromatography on CPC employing CHCl$_3$-iPr$_2$-NH-MeOH-H$_2$O (7:1:6:4, lower phase stationary) afforded pure batzelline B (2, 0.038%) and C (3, 0.018%).

The aqueous layer was lyophilized and extracted with MeOH (200 ml) to give 2.7 g of brown solid. Subsequent solvent partition of the latter extract using 13:7:8 CHCl$_3$-MeOH-H$_2$O, followed by centrifugal countercurrent chromatography of the resulting lower layer using CPC 2:7:6:3 heptane-CHCl$_3$-MeOH-H$_2$O (lower phase stationary) yielded isobatzelline A (0.018%), B (0.028%), and C (0.021%). The resulting stationary phase was further purified by CPC (4:7:4:3 heptane-EtOAc-MeOH-H$_2$O, lower phase stationary) to give isobatzelline D (0:025%) as a brown solid.

A second collection (817 g) of Batzella sp. was also repeatedly extracted with 2:1 methanol-chloroform (1 1×3). Removal of solvents in vacuo gave 42 g of concentrated extract which was partitioned using 15:2:15 CHCl$_3$-MeOH-H$_2$O (1.6 L) into two fractions, an upper layer (32 g) and a lower layer (10 g). Repeated countercurrent chromatography of both fractions in a fashion similar to those for the extracts from the first collection also yielded batzellines A, B, C and isobatzellines A, B, C, and D.

EXAMPLE 2—PHYSICAL AND SPECTRAL DATA OF BATZELLINE A

Batzelline A was obtained as a dark brown solid, purple in solution. Recrystallization from chloroform-/methanol gave black prisms;

mp.=205° C.

HREIMS m/z 282.0224 (calcd. for M$^+$=C$_{12}$H$_{11}$N$_2$O$_2$SCl, Δ0.6 mmu);

LREIMS m/z 284 (31), 282 (75), 269 (3), 267 (3), 256 (9), 254 (24), 247 (19), 241 (11), 239 (31), 232 (6), 211 (14), 209 (17), 198 (6), 176 (8), 161 (3), 141 (3), 127 (4), 103 (4), and 88 (3 rel. %);

UV (MeOH) λ$_{max}$, 214 (ε8,900), 269 (ε22,100), 356 (ε7,900), 376 (ε8,000), and 548 (ε600) nm;

IR (KBr) 3420, 1667, 1588, 1560, 1525, 1427, 1349, 1309, 1253, 1229, 1192, 1161, 1081, 1000, 976, 838, and 726 cm$^{-1}$;

$^1$H NMR (DMSO-d$_6$): δ8.34 (1H, br s, D$_2$O exchangeable), 3.87 (3H, s), 3.60 (2H, dt, J=2.6, 7.0 Hz), 2.80 (2H, t, J=7.0 Hz), and 2.36 (3H, s);

$^{13}$C NMR (DMSO-d$_6$): δ170.9 (s), 168.6 (s), 148.4 (s), 132.3 (s), 124.8 (s), 121.9 (s X 2), 97.1 (s), 41.5 (t), 32.7 (q), 19.1 (t), and 18.0 (q).

The structure of batzelline A is shown below:

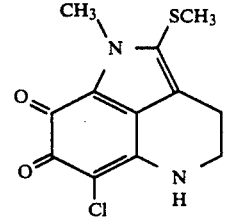

EXAMPLE 3—PHYSICAL AND SPECTRAL DATA OF BATZELLINE B

A dark brown solid;

HREIMS m/z 268.0062 (calcd. for M$^+$=C$_{11}$H$_9$N$_2$O$_2$S$^{35}$Cl, Δ1.1 mmu);

LREIMS m/z 270 (54), 268 (100 rel. %), 257 (8), 253 (25), 242 (14), 240 (37), 235 (11), 233 (19), 227 (32), 225 (86), 199 (16), 197 (37), 170 (10), 161 (12), 149 (7), 134 (14), 58 (40), 43 (100), and 31 (95);

UV (MeOH) $\lambda_{max}$ 211 ($\epsilon$58,300), 266 ($\epsilon$120,800), 330 (sh), 387 ($\epsilon$51,800), and 550 ($\epsilon$4,000) nm;

$^1$H NMR (DMSO-$d_6$): $\delta$12.85 (1H, brs), 8.35 (1H, brs), 3.60 (2H, td, J=7.0, 1.7 Hz), 2.72 (2H, t, J=7.0 Hz), and 2.49 (3H, s);

$^{13}$C NMR (DMSO-$d_6$): $\delta$171.7 (s), 167.3 (s), 148.7 (s), 131.3 (s), 125.1 (s), 123.5 (s), 119.7 (s), 97.0 (s), 41.6 (t), 18.7 (t), and 17.3 (q).

The structure of batzelline B is shown below:

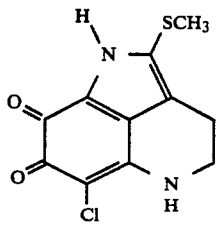

EXAMPLE 4—PHYSICAL AND SPECTRAL DATA OF BATZELLINE C

A dark brown solid;

HREIMS m/z 236.0350 (calcd. for $C_{11}H_9N_2O_2{}^{35}Cl$, $\Delta$0.3 mmu);

LREIMS m/z 238 (10), 236 (16), 223 (2), 210 (5), 208 (15), 201 (6), 180 (2), 145 (5), 118 (7), 101 (20), 86 (100 rel. %), and 58 (35);

UV (MeOH $\lambda_{max}$ 211 ($\epsilon$7,900), 250 ($\epsilon$17,300), 331 ($\epsilon$9,100), 380 (sh), and 540 ($\epsilon$900) nm;

$^1$H NMR (DMSO-$d_6$): $\delta$8.28 (1H, brs), 7.14 (1H, s), 3.82 (3H, s), 3.56 (2H, dt, J=1.9, 7.0 Hz), and 2.73 (2H, t, J=7.0 Hz);

$^{13}$C NMR (DMSO-$d_6$): $\delta$171.4 (s), 169.1 (s), 148.9 (s), 129.4 (d), 123.4 (s), 122.9 (s), 116.7 (s), 96.9 (s), 41.7 (t), 35.5 (q), and 18.9 (t).

The structure of batzelline C is shown below:

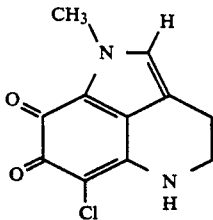

EXAMPLE 5—PHYSICAL AND SPECTRAL DATA OF ISOBATZELLINE A

A brown solid, mp. (dec.);

HRFABMS: MH+282.0482 (calcd. for $C_{12}H_{13}ON_3{}^{35}ClS$, $\Delta$mmu 1.4);

LREIMS: 283/281 (42/100), 266/264 (29/53), 248 (15), 233 (23), 221 (13), 205 (21), 191 (6), 180 (6), and 161 (5);

UV (MeOH): 262 ($\epsilon$15,500), 342 (9,000), and 430 nm (3,100);

IR (KBr): 3460, 3340, 2930, 1640, 1580, 1560, 1435, 1400, 1380, 1350, 1295, 1070, and 965 cm$^{-1}$;

$^1$H NMR (DMSO-$d_6$): $\delta$2.39 (3H, s), 3.93 (3H, s), 2.99 (2H, t, J=7.3 Hz), 3.95 (2H, t, J=7.3 Hz);

$^{13}$C NMR (DMSO-$d_6$): $\delta$18.5 (q), 19.3 (t), 33.9 (q), 43.8 (t), 94.1 (s), 121.6 (s), 124.3 (s), 124.6 (s), 137.1 (s), 152.5 (s), 154.0 (s), 165.8 (s).

The structure of isobatzelline A is shown below:

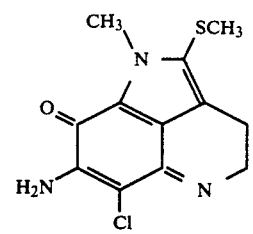

EXAMPLE 6—PHYSICAL AND SPECTRAL DATA OF ISOBATZELLINE B

A reddish brown solid, mp. (dec);

HREIMS: M+247.0780 (calcd. for $C_{12}H_{13}ON_3S$, $\Delta$mmu 0.1):

LREI: 247 (100), 231 (24), 214 (15), 199 (35), 187 (13), 174 (10), and 149 (10);

UV (MeOH): 264 ($\epsilon$14,200), 362 (7,000), and 402 (5,000);

IR (KBr): 3430, 3080, 2930, 1655, 1600, 1525, 1390, 1300, 1250, 1140, 1050, 956, and 845 cm$^{-1}$;

$^1$H NMR (DMSO-$d_6$): $\delta$2.33 (3H, s), 2.84 (2H, t, J=7.5 Hz), 3.89 (2H, t, J=7.5 Hz), 3.96 (3H, s), 5.69 (1H, s);

$^{13}$C NMR (DMSO-$d_6$): $\delta$18.5 (q), 19.6 (t), 33.7 (q), 43.6 (t), 88.0 (d), 122.8 (s), 124.2 (s), 125.9 (s), 136.4 (s), 157.3 (s), 158.7 (s), 168.8 (s).

The structure of isobatzelline B is shown below:

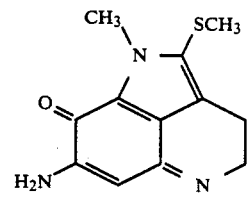

EXAMPLE 7—PHYSICAL AND SPECTRAL DATA OF ISOBATZELLINE C

A greenish brown solid, mp. (dec);

HREIMS: M+235.0510 (calcd. for $C_{11}H_{10}ON_3{}^{35}Cl$, $\Delta$mmu 0.2);

LREIMS: 237/235 (36/100), 222 (8), 208 (27), 201 (84), 173 (34), 145 (45), and 129 (27);

UV (MeOH): 244 ($\epsilon$9,700), 344 (5,900), 394 (2,600);

IR (KBr): 3360, 3050, 1670, 1600, 1420, 1340, 1320, 1200, 1135, 835, 804, and 720 cm$^{-1}$;

$^1$H NMR (DMSO-$d_6$): $\delta$2.96 (2H, t, J=7.5 Hz), 3.91 (2H, t, J=7.5 Hz), 3.93 (3H, s), 7.13 (1H, s);

$^{13}$C NMR (DMSO-$d_6$): $\delta$19.21 (t), 36.6 (q), 44.3 (t), 93.9 (s), 120.3 (s), 122.8 (s), 124.1 (s), 132.4 (d), 153.5 (s), 155.1 (s), 166.8 (s).

The structure of isobatzelline C is shown below:

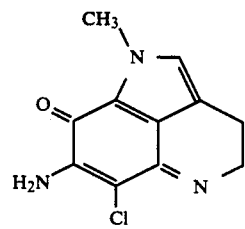

EXAMPLE 8—PHYSICAL AND SPECTRAL DATA OF ISOBATZELLINE D

A reddish brown solid, mp. (dec);

HREIMS: M+279.0230 (calcd. for $C_{12}H_{10}N_3OS^{35}Cl$, Δmmu 0.3);

LREIMS: 281/279 (38/100), 266/264 (25/72), 246 (18), 232 (23), 220 (11), 196 (11), 186 (7), 173 (9), 159 (6);

IR (KBr): 3450, 3310, 2930, 1640, 1560, 1545, 1485, 1440, 1400, 1340, 1320, 1290, 1250, 1145, 1080, and 960 cm$^{-1}$;

UV (MeOH): 239 (ε33,900), 263 (25,000), and 439 nm (25,200);

$^1$H NMR(DMSO-d$_6$): δ2.79 (3H, s), 4.22 (3H, s), 6.44 (2H, s, D$_2$O exchangeable), 7.64 ($^1$H, d, J=5.8 Hz), 8.34 (1H, d, J=5.8 Hz);

$^{13}$C NMR(DMSO-d$_6$): δ17.5 (q), 34.5 (q), 103.9 (s), 112.0 (d), 116.5 (s), 118.8 (s), 125.5 (s), 138.6 (s), 141.4 (d), 143.8 (s), 146.4 (s), 163.3 (s).

The structure of isobatzelline D is shown below:

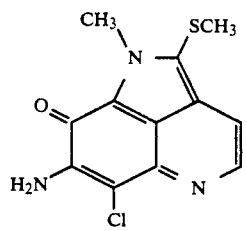

EXAMPLE 9—METHYLATED DERIVATIVE OF BATZELLINE A

Batzelline A (9.5 mg) was refluxed with CH$_3$I (5 ml) and K$_2$CO$_3$ (50 mg) in 5 ml of CHCl$_3$ at 70° C. overnight. The product was separated on Hibar NH$_2$ HPLC column (20:1 CHCl$_3$/MeOH) to give 9.4 mg of pure methylated batzelline A, a greenish solid.

HREIMS m/z 296.0386 (calcd. for M+=$C_{13}H_{13}N_2O_2S^{35}Cl$, Δ0.1 mmu);

LREIMS m/z 298 (17), 296 (36), 285 (66), 270 (5), 268 (13), 262 (18), 261 (28), 255 (10), 253 (27), 246 (10), 234 (8), 223 (4), 219 (17), 217 (6), 212 (6), 191 (4), 190 (8), 189 (7), 184 (4), 175 (3), 149 (5), 134 (6), 85 (17), 83 (27), 52 (23), 50 (75), 38 (40), and 36 (100 rel. %);

$^1$H NMR(CDCl$_3$): δ3.92 (3H, s), 3.64 (2H, t, J=6.9 Hz), 3.62 (3H, s), 2.81 (2H, t, J=7.0 Hz), and 2.33 (3H, s);

$^{13}$C NMR(CDCl$_3$): δ174.1 (s), 167.9 (s), 148.2 (s), 132.2 (s), 125.1 (s), 124.1 (s), 122.5 (s), 100.6 (s), 54.9 (q), 42.8 (t), 33.0 (q), 20.1 (t), and 18.7 (q).

EXAMPLE 10—HYDROGENATED DERIVATIVE OF BATZELLINE A

Batzelline A (7.5 mg) was hydrogenated with 70 mg of 10% Pd/C in 5 ml of CHCl$_3$ under 50 psi at room temperature overnight. The product was separated on a Hibar NH$_2$ HPLC column (15:1 CHCl$_3$/MeOH) to give 2.3 mg of pure hydrogenated product, a brown solid.

HREIMS m/z 202.0742 (calcd. for M+=$C_{11}H_{10}N_2O_2$, Δmmu);

LREIMS m/z 202 (98), 201 (47), 174 (28), 155 (13), 145 (22), 119 (60), 104 (17), 91 (14), 89 (12), 85 (10), 83 (16), 79 (15), 77 (23), 63 (13), 57 (11), 51 (22), and 42 (38 rel. %);

$^1$H NMR(DMSO-d$_6$): δ8.18 (1H, brs, D$_2$O exchangeable), 7.07 (1H, s), 5.02 (1H, s), 3.82 (3H, s), 3.47 (2H, dt, J=2.5, 6.9 Hz), and 2.69 (2H, t, J=6.9 Hz);

$^{13}$C NMR(DMSO-d$_6$): δ177.7 (s), 171.5 (s), 153.7 (s), 128.6 (d), 124.3 (s), 123.9 (s), 116.0 (s), 92.5 (d), 41.1 (t), 35.4 (q), and 19.0 (t).

EXAMPLE 11—METHYLATED DERIVATIVE OF BATZELLINE B

Batzelline B (2.5 mg) was methylated by refluxing with CH$_3$I (5 ml) and K$_2$CO$_3$ (50 mg) in CHCl$_3$ (5 ml) at 70° C. refluxing overnight to yield the desired product (3.0 mg).

EXAMPLE 12—HYDROGENATED DERIVATIVE OF BATZELLINE C

Hydrogenation of Batzelline C (2.5 mg) with 10% Pd/C (30 mg) in 1.5 ml of 2:1 MeOH/CHCl$_3$ at room temperature for 3 hours gave the desired product (1.8 mg).

EXAMPLE 13—HYDROGENATED DERIVATIVE OF ISOBATZELLINE A, B, AND C

A suspension of 25 mg of isobatzelline A and 10 mg of 10% Pd/C in 10 ml of MeOH was agitated under 30 psi hydrogen at room temperature for 16 hours. After removal of the catalyst and the solvent, the reddish brown solid was separated on a Hibar NH$_2$ HPLC column to give 6 mg of the reduced product, as a greenish brown solid, mp. (dec).

HRFABMS: MH+202.0994 (calcd. for $C_{11}H_{11}ON_3$, Δ1.4 mmu);

LREIMS: 201 (100), 174 (34), 145 (16), 119 (11), 105 (29), 91 (39), and 77 (17);

UV (MeOH): 244 (ε14,200), 346 (8,500), and 392 nm (4,000);

IR (KBr): 3400, 2930, 1660, 1605, 1430, 1360, 1350, 1320, 1255, 1205, 1100, 835, and 800 cm$^{-1}$;

$^1$H NMR(1:2 CDCl$_3$-CD$_3$OD): δ2.86 (2H, t, J=7.6 Hz), 3.82 (2H, t, J=7.6 Hz), 3.94 (3H, s), 5.63 (1H, s), and 7.00 (1H, s).

Isobatzelline B and C can also be reduced using the procedures described above.

EXAMPLE 14—CONVERSION OF ISOBATZELLINE A TO BATZELLINE A

A solution of 20 mg of isobatzelline A in 2 ml of HOAc and 1 ml of dioxane is allowed to react with 20 mg of NaNO$_2$ in 5 ml of H$_2$O at 0° C. for 2 hours. After addition of 3 ml of 1N HCl, the solution was stirred at room temperature overnight, and extracted with 10 ml CHCl$_3$/MeOH (1:1) twice. The concentrated extract was further fractionated on a Superco LC-NH$_2$ column (50 ml×3 ml) with 1% MeOH/CHCl$_3$, and subsequently purified on a HPLC LiChrosorb-NH$_2$ column (3% MeOH/CHCl$_3$) to give 4 mg of batzelline A.

EXAMPLE 15—CONVERSION OF ISOBATZELLINE A TO ISOBATZELLINE D

A solution of 10 mg of isobatzelline A in 5 ml of dioxane was stirred with 10 mg of DDQ at room temperature overnight. The resulting product was purified by HPLC (LiChrosorb NH$_2$, 3% MeOH-CHCl$_3$) to give 6 mg of isobatzelline D.

EXAMPLE 16—ANTIFUNGAL PROPERTIES

A. Protocol

1. Preparation of inocula

All media were autoclaved at 121° C. for 15 minutes. *Candida albicans*: *C. albicans* (ATCC strain 44506) was grown on Sabouraud dextrose agar to produce single colonies, one of which was used to inoculate Sabouraud dextrose broth. The broth was incubated at 37° C. with shaking at 200 rpm for 18 hours. The resultant culture was brought to 10% (v/v) glycerol, frozen at −80° C., and used as the inoculum for the anti-Candida assay. *Aspergillus nidulans*: *A. nidulans* (ATCC strain 36321) was grown from a spore stock on the surface of a YAG plate (YAG: yeast extract 0.5%; glucose 2%; agar 2%) at 30° C. until the colony sporulated; at this point the colony was green (usually within one week). Spores were harvested by washing with 0.1% (v/v) TRITON TM X-100. Spores were then washed with distilled water before freezing at −80° C. in the presence of 10% (v/v) glycerol. *Bacillus subtilis*: Standard spore stocks (ATCC strain 6633) were purchased from Difco (#0453-36-0). *Escherichia coli*: The BMR strain was used. This was grown overnight with shaking at 37° C. in nutrient broth and frozen in 1 mL aliquots in the presence of 10% (v/v) glycerol at −80° C. *Pseudomonas aeruginosa*: (ATCC strain 27853) Grown and stored as described for *E. coli*.

2. Assay protocols i. Disc diffusion assay

*C. albicans* was inoculated into either melted Sabouraud dextrose agar or Roswell Park Memorial Institute medium 1640 (RPMI-1640) in 2% agar at 45° C. to give a cell density of approximately 10,000 cells/mL. Plates were prepared with 10 mL of the needed agar in a 10 cm × 10 cm petri dish. These plates were stored at 4° C. until needed for the assay.

*A. nidulans* spores were inoculated at 10,000/mL into melted YAG cooled to 45° C. Bacteria were inoculated into melted Penassay agar at a density of 10,000/ml. Plates were poured as described above.

Paper discs (6.35 mm) were impregnated with the test substance and allowed to dry. They were then placed onto the surface of a test plate prepared as detailed above. Plates were incubated overnight (*C. albicans*, *B. subtilis*, *E. coli*, and *P. aeruginosa* 37° C.; and *A. nidulans* 30° C.) after which time the zones of growth inhibition could be read. These are expressed as the diameter of the zone in millimeters. Standard drugs were used in all cases.

3. MIC protocol

Two-fold dilutions of the drug/extract were prepared in 50 µL volumes of a suitable solvent using 96-well microtiter plates. A 25% mixture of MeOH in water was generally used; however, EtOH, 5% EtOAc in EtOH, DMSO, or other compatible solvents could be substituted if necessary. In a separate 96-well plate, 35 µL volumes of either Sabouraud dextrose broth or RPMI-1640 were placed in each well. The drug/extract (5 µL) was then transferred to the broth using a 12-place pipettor. An inoculum of *C. albicans* in the appropriate medium was added to give a cell density of 1000 cells/mL and a total volume of 50 µL. If DMSO was used as solvent a total volume of 100 µL was used so that the DMSO level did not exceed 5%. SDB plates were incubated at 37° C. overnight, RPMI-1640 plates were incubated at 37° C. in a humidified atmosphere of 10% $CO_2$. 10 µL of triphenyl tetrazolium chloride (1% w/v; filter sterilized) was then added to each well; a further 2 hour incubation resulted in a deep coloration of the microorganism. The MIC is the lowest concentration of the drug which has completely inhibited growth.

B. Results

The compounds of the subject invention inhibit the growth of fungi such as *Candida albicans*. The antifungal activity may be of use in the treatment of fungal diseases of humans, animals, and possibly plants. Formulations may be for either topical or systemic use.

Activities of the compounds were as follows:

TABLE 1

| Isobatzelline | *C. albicans* MIC (µg/ml) |
|---|---|
| A | 3.1 |
| B | 25.0 |
| C | 50.0 |
| D | 25.0 |

EXAMPLE 17—P388 MOUSE LEUKEMIA CELL ASSAY

A. Maintenance of Cell Line

P388 murine leukemia cells obtained from Dr. J. Mayo, National Cancer Institute, Bethesda, Md., were maintained in Roswell Park Memorial Institute medium 1640 (RPMI-1640) supplemented with 10% horse serum and cultured in plastic tissue culture flasks and kept in an incubator at 37° C. in humidified air containing 5% $CO_2$. Antibiotic-free stock cultures of P388 cells were subcultured to $10^5$ cells/ml by dilutions in fresh growth medium at 2 to 5 day intervals.

B. Procedure

To assess the antiproliferative effects of agents against P388 cells, 200 µl cultures (96-well tissue culture plates, Nunc, Denmark) were established at $1 \times 10^5$ cells/ml in drug-free medium containing agents at various concentrations. After 48 hour exposures, P388 cells were enumerated using 3-[4,5-dimethylthiazol-2-yl]-2,5-diphenyltetrazolium bromide (MTT) as described below.

To quantitate the effects of agents on cell proliferation, 75 µl warm growth medium containing 5 mg/ml MTT was added to each well. Cultures were returned to the incubator and left undisturbed for 90 minutes. To spectrophotometrically quantitate formation of reduced formazan, plates were centrifuges (900 g, 5 minutes), culture fluids were removed by aspiration, and 200 µl of acidified isopropanol (2 ml concentrated HCl/L isopropanol) added per well. The absorbance of the resulting solutions were measured at 570 nm with a plate reader (MR700 Microplate Reader, Dynatech Laboratories, Chantilly, Va.). The absorbance of test wells was divided by the absorbance of drug free wells, and the concentration of the agent that resulted in 50% of the absorbance of untreated cultures was determined by linear regression of logit-transformed data. A linear relationship between P388 cell number and formazan production was found over the range of cell densities observed in this study.

Analogous procedures were followed for the A549 and HT29 cell lines.

C. Results

As shown in Table 2, the compounds of the subject invention show cytotoxic activity in the P388, A549, and HT29 assays. These compounds, or compositions containing these compounds, may be used for inhibiting the growth of tumor or cancer cells.

TABLE 2

|  | IC$_{50}$ ($\mu$g/ml) | | |
| --- | --- | --- | --- |
|  | P388 | A549 | HT29 |
| Isobatzelline A | 0.42 | 0.07 | 0.44 |
| Isobatzelline B | 2.6 | 2.8 | 2.5 |
| Isobatzelline C | 12.6 | >20.0 | 10.0 |
| Isobatzelline D | 20.0 | >20.0 | >20.0 |

EXAMPLE 18—ANTIMICROBIAL PROPERTIES

Isobatzelline A has also been shown to inhibit the growth of *B. subtilis*. Thus, these compounds may also be used as antimicrobial agents.

EXAMPLE 19—FORMULATION AND ADMINISTRATION

The compounds of the invention are useful for various non-therapeutic and therapeutic purposes. It is apparent from the testing that the compounds of the invention are effective for inhibiting fungal growth and for controlling tumor growth. Also, because of the antifungal properties of the compounds, they are useful to swab laboratory benches and equipment in a microbiology laboratory to eliminate the presence of fungi, or they can be used as ultraviolet screeners in the plastics industry since they effectively absorb UV rays. As disclosed herein, they are also useful prophylactically and therapeutically for treating fungal infections in animals and humans.

Therapeutic application of the new compounds and compositions containing them can be contemplated to be accomplished by any suitable therapeutic method and technique presently or prospectively known to those skilled in the art. Further, the compounds of the invention have use as starting materials or intermediates for the preparation of other useful compounds and compositions.

The dosage administration to a host in the above indications will be dependent upon the identity of the infection, the type of host involved, its age, weight, health, kind of concurrent treatment, if any, frequency of treatment, and therapeutic ratio.

The compounds of the subject invention can be formulated according to known methods for preparing pharmaceutically useful compositions. Formulations are described in detail in a number of sources which are well known and readily available to those skilled in the art. For example, *Remington's Pharmaceutical Science* by E. W. Martin describes formulations which can be used in connection with the subject invention. In general, the compositions of the subject invention will be formulated such that an effective amount of the bioactive compound(s) is combined with a suitable carrier in order to facilitate effective administration of the composition.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A compound having the following structure

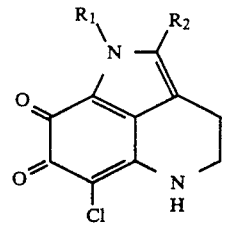

wherein R$_1$ can be CH$_3$ or H; and R$_2$ can be SCH$_3$ or H.

2. The compound, according to claim 1, wherein R$_1$ is CH$_3$ and R$_2$ is SCH$_3$.

3. The compound, according to claim 1, wherein R$_1$ is H and R$_2$ is SCH$_3$.

4. The compound, according to claim 1, wherein R$_1$ is CH$_3$ and R$_2$ is H.

5. A compound having the following structure:

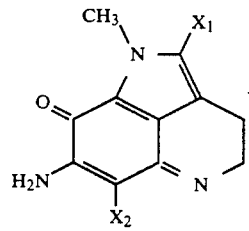

wherein X$_1$ can be SCH$_3$ or H; and X$_2$ can be Cl or H.

6. The compound, according to claim 5, wherein X$_1$ is SCH$_3$ and X$_2$ is Cl.

7. The compound, according to claim 5, wherein X$_1$ is SCH$_3$ and X$_2$ is H.

8. The compound, according to claim 5, wherein X$_1$ is H and X$_2$ is Cl.

9. The compound, according to claim 5, wherein X$_1$ is H and X$_2$ is H.

10. A compound having the following structure:

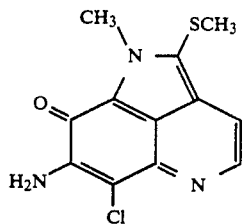

11. A process for inhibiting the growth of P388 Leukemic cells, said process comprising administering to said cells an effective amount of a compound of claim 5.

12. A process for inhibiting the growth of P388 Leukemic cells, said process comprising administering to said cells an effective amount of the compound of claim 10.

13. A process for inhibiting fungal growth, said process comprising applying to said fungus and effective amount of a compound of claim 5.

14. A process for inhibiting fungal growth, said process comprising applying to said fungus an effective amount of the compound of claim 10.

15. A process for inhibiting the growth of bacteria, said process comprising administering to said bacteria an effective amount of the compound of claim 7.

16. A pharmaceutical composition comprising a compound of claim 1, 5 or 10 and a pharmaceutically adequate carrier.

* * * * *

UNITED STATES PATENT AND TRADEMARK OFFICE
CERTIFICATE OF CORRECTION

PATENT NO. : 5,028,613

DATED : July 2, 1991

INVENTOR(S) : H. Howard Sun, Shinichi Sakemi

It is certified that error appears in the above-identified patent and that said Letters Patent is hereby corrected as shown below:

On the title page:

| | |
|---|---|
| [75] Inventors: | "Shin-ishi" should read --Shinichi--. |
| [73] Assignee: | "Repligen Corporation, Cambridge, Mass." should read --Harbor Branch Oceanographic Institution, Inc., Fort Pierce, Florida--. |
| Column 3: | lines 67 & 68 "batzelline" should read --batzellines--. |
| Column 4: | lines 6-7: "CPC 2:7:6:3 heptane-$CHCl_3$-MeOH-$H_2O$ (lower phase stationary)" should read --CPC (2:7:6:3 heptane-$CHCl_3$-MeOH-$H_2O$; lower phase stationary)--. |
| Column 7: | line 38: "Hibar" should read --a Hibar--. |
| Column 12: | line 58: "and" should read --an--. |
| Column 3: | line 52: "methanolchloroform" should read --methanol-chloroform--. |
| Column 5: | line 55: "CIS" should read --ClS--. |
| Column 7: | line 43: "285 (66)" should read --285 (2), 283 (66)--. |
| Column 10: | line 52: "centrifuges" should read --centrifuged--. |
| Column 12: | lines 66-67: "adequate" should read --acceptable--. |

Signed and Sealed this

Ninth Day of March, 1993

*Attest:*

STEPHEN G. KUNIN

*Attesting Officer*     *Acting Commissioner of Patents and Trademarks*